United States Patent
Johnson et al.

(12)

(10) Patent No.: US 11,224,441 B2
(45) Date of Patent: Jan. 18, 2022

(54) TOURNIQUET

(75) Inventors: Ross Johnson, Anderson, SC (US); Richard A. Hester, Greenville, SC (US)

(73) Assignee: Tactical Medical Solutions, LLC, Anderson, SC (US)

( * ) Notice: Subject to any disclaimer, the term of this patent is extended or adjusted under 35 U.S.C. 154(b) by 0 days.

(21) Appl. No.: 12/964,294

(22) Filed: Dec. 9, 2010

(65) Prior Publication Data

US 2011/0307004 A1 Dec. 15, 2011

Related U.S. Application Data

(60) Provisional application No. 61/285,157, filed on Dec. 9, 2009.

(51) Int. Cl.
*A61B 17/132* (2006.01)
*A61F 13/00* (2006.01)

(52) U.S. Cl.
CPC ...... *A61B 17/1322* (2013.01); *A61B 17/1327* (2013.01); *A61F 2013/00468* (2013.01)

(58) Field of Classification Search
CPC ........ A61F 5/37; A61F 5/3715; A61F 5/3723; A61F 5/373; A61F 5/3738; A61F 5/3753; A61F 5/3761; A61F 5/3769; A61F 5/3776; A61F 5/30; A61F 5/32; A61F 5/34; A44B 11/00; A44B 11/006; A44B 11/02; A44B 11/06; A44B 11/065; A44B 11/08; A44B 11/10; A44B 11/12; A44B 11/125; A44B 11/18; A61B 17/132; A61B 17/1322; A61B 17/1325; A61B 17/1327; A61B 17/135; A61B 17/1355

USPC .................................. 600/499; 606/201–204
See application file for complete search history.

(56) References Cited

U.S. PATENT DOCUMENTS

| | | |
|---|---|---|
| 1,855,482 A | 4/1932 | McArthur |
| 2,084,412 A | 6/1937 | Schaefer |
| 2,250,977 A | 7/1941 | Walker |
| 2,387,428 A | 10/1945 | Brothers |
| 2,410,880 A | 11/1946 | Hennicke |
| 2,480,430 A | 8/1949 | Walters |
| 2,528,078 A | 10/1950 | Cuthbert |
| D185,635 S | 7/1959 | Gerlach |
| 3,120,846 A | 2/1964 | Fletcher |
| 3,165,803 A | 1/1965 | Gaylord |

(Continued)

FOREIGN PATENT DOCUMENTS

| | | |
|---|---|---|
| DE | 3327528 | 2/1985 |
| DE | 3327528 A1 * | 2/1985 |

(Continued)

*Primary Examiner* — Brooke Nicole Labranche
(74) *Attorney, Agent, or Firm* — Cahn & Samuels, LLP

(57) ABSTRACT

The present invention relates generally to first aid articles and more specifically to tourniquets suitable for one handed application. One embodiment of the invention is directed to a tourniquet having a base defining first and second ends. A constricting band is attached to and extends from the first end of the base. A handle is engaged with the constricting band. The constricting band engages a self cinching buckle which includes polygonal frame member and a self cinching member engaged with the polygonal frame member. A hook member is attached to the first end of the base and is configured to engage the polygonal frame member.

23 Claims, 5 Drawing Sheets

(56) References Cited

U.S. PATENT DOCUMENTS

| | | | |
|---|---|---|---|
| D260,074 S | 8/1981 | Lewis | |
| 4,501,027 A | 2/1985 | Olsson | |
| 4,549,550 A * | 10/1985 | Kami | 600/499 |
| 4,551,889 A * | 11/1985 | Narayan et al. | 24/196 |
| 4,610,056 A * | 9/1986 | Emmert | A44B 11/12 |
| | | | 24/193 |
| 4,778,033 A * | 10/1988 | Gonzalez | A62B 35/0031 |
| | | | 128/878 |
| 4,794,656 A | 1/1989 | Henley, Jr. | |
| 1,406,770 A | 2/1992 | Philip | |
| D324,328 S | 3/1992 | Pagan | |
| 5,607,448 A | 3/1997 | Stahl et al. | |
| D385,178 S | 10/1997 | Poulin | |
| 5,993,362 A | 11/1999 | Ghobadi | |
| 6,298,521 B1 | 10/2001 | Butterfield | |
| 6,540,707 B1 | 4/2003 | Stark et al. | |
| 6,544,188 B1 | 4/2003 | Chesney et al. | |
| 6,602,214 B2 | 8/2003 | Heinz et al. | |
| 6,746,470 B2 * | 6/2004 | McEwen et al. | 606/202 |
| 6,899,720 B1 | 5/2005 | McMillan | |
| D516,901 S | 3/2006 | Murray | |
| D527,981 S | 9/2006 | Sato | |
| D545,663 S | 7/2007 | Sato | |
| D592,484 S | 5/2009 | Ricereto | |
| 7,776,064 B2 | 8/2010 | Johnson et al. | |
| 7,842,067 B2 | 11/2010 | Esposito | |
| 7,892,253 B2 * | 2/2011 | Esposito et al. | 606/203 |
| 2003/0028215 A1 | 2/2003 | Brooks | |
| 2005/0113866 A1 | 5/2005 | Heinz et al. | |
| 2005/0240217 A1 * | 10/2005 | Jennifer | A61B 17/1322 |
| | | | 606/203 |
| 2005/0267518 A1 | 12/2005 | Wright et al. | |
| 2006/0095072 A1 * | 5/2006 | TenBrink et al. | 606/201 |
| 2006/0185131 A1 * | 8/2006 | Anderson | A44B 11/006 |
| | | | 24/171 |
| 2007/0005107 A1 | 1/2007 | Janota | |
| 2008/0148533 A1 * | 6/2008 | Calkin | A41F 9/02 |
| | | | 24/302 |
| 2008/0183207 A1 | 7/2008 | Horne | |
| 2008/0221612 A1 | 9/2008 | Rose | |
| 2009/0024159 A1 | 1/2009 | Nee et al. | |
| 2009/0062842 A1 | 3/2009 | Esposito et al. | |
| 2010/0057120 A1 * | 3/2010 | Kirkham | A61B 17/1322 |
| | | | 606/203 |
| 2010/0137900 A1 | 6/2010 | Chao | |
| 2010/0234877 A1 * | 9/2010 | Pienkowski et al. | 606/203 |
| 2011/0270299 A1 * | 11/2011 | Rose | A61B 17/1322 |
| | | | 606/203 |

FOREIGN PATENT DOCUMENTS

| | | | |
|---|---|---|---|
| FR | 927002 A | 10/1947 | |
| GB | 611794 A * | 11/1948 | A44B 11/10 |
| JP | S59232531 | 12/1984 | |
| JP | 7051275 | 2/1995 | |
| NZ | WO 2005090207 A1 * | 9/2005 | A44B 11/02 |
| WO | 2005090207 A | 9/2005 | |
| WO | 2006071251 A2 | 7/2006 | |

* cited by examiner

TOURNIQUET

CROSS-REFERENCES TO OTHER RELATED PATENT APPLICATIONS

This application claims priority from application Ser. No. 61/285,157 filed Dec. 9, 2009, which is incorporated herein by reference in its entirety.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISK APPENDIX

Not Applicable.

BACKGROUND OF THE INVENTION

1. Field of the Invention

The present invention relates to medical devices used in first aid. More specifically, this invention relates to improvements in tourniquets used for emergency medical use.

2. Description of Related Art

Loss of blood is a major cause of death in emergency situations in which the injured person is alone or medical assistance is not immediately available. The use of a tourniquet to stop blood loss from an injured arm or leg is a well-known technique for stopping blood flow in these situations. In general, for emergency use where the victim is alone, the victim must be able to apply the tourniquet to his or her own arm or leg and occlude blood flow using only one hand. A typical tourniquet is a tightly tied or wound band applied around a body part, e.g., an arm or a leg, in an attempt to stop severe bleeding or uncontrolled hemorrhage in an emergency situation.

In recent years, several tourniquets designed for one-handed application have become available. These tourniquets typically include a strap 10 engaged with a substantially rigid base 15 and threaded through or looped around a handle 20 as illustrated in FIG. 1. In order to tighten the tourniquet around a limb, strap 10 is threaded through buckle 25 and handle 20 is twisted thereby causing strap 10 to constrict circumferentially about the limb. A significant drawback to these known tourniquets is, under certain circumstances, they do not facilitate speedy deployment to trapped limbs. In order to deploy these tourniquets to trapped limbs, strap 10 must be manually disengaged from the buckle 25 and subsequently routed around the limb and reengaged with buckle 25 before being tightened. That process requires acute concentration as well as precise dexterity, characteristics that are often not available to an injured person in crisis or a first responder in a high stress environment. In addition, that process delays tourniquet application where even a few seconds of delay can cause fatal blood loss.

Another drawback of known tourniquets designed for one-handed application is that they are sometimes difficult to cinch even when the strap is engaged with the buckle requiring several tugs on the strap and sometimes aid of a second hand. Often, it necessary for an injured person to apply the tourniquet to its own limb. The injured person may have suffered severe trauma and may not have the presence of mind, the patience or the stamina to overcome cinching difficulties.

The use of a tourniquet by military personnel, law enforcement personnel and first responders imposes weight and size restrictions. Such personnel carry a variety of critical equipment and they will be disinclined to carry a tourniquet if it is too heavy or if it is too bulky. Accordingly, there is a need for a lightweight, low profile tourniquet that can be rapidly applied by a first responder or by the victim using one hand.

BRIEF SUMMARY OF THE INVENTION

It is an object of the present invention to provide a lightweight, compact tourniquet suitable for one handed application.

It is a further object of the invention to provide a tourniquet suitable for one handed application that can be easily applied to trapped limbs.

It is another object of the invention to provide a tourniquet suitable for one handed application that minimizes undesired loosening.

Still another object of the invention is to provide tourniquet suitable for one handed application that minimizes unintended disengagement.

It is still a further object of the invention to provide a tourniquet suitable for one handed application that provides an audible alert when the tourniquet is properly deployed.

In accordance with an embodiment of the invention, a tourniquet comprises a base having first and second ends, a constricting band attached to and extending from the first end of the base and a handle engaged with the constricting band. A self cinching buckle includes a polygonal frame member and a self cinching member engaged with the frame member and a free end of the constriction band is threaded through the self cinching buckle. A hook member is attached to the first end of the base and configured to engage said frame member.

In accordance with another embodiment of the invention, a locking assembly for a tourniquet comprises In another embodiment, a locking ring is attached to the structural member.

In further embodiment of the invention, at least one of the first and second ends of the handle is configured to engage with the locking ring.

In yet another embodiment of the invention, the locking ring is operatively associated with the handle and at least one of the first and second ends of the handle includes a latching section that engages the locking ring.

In still another embodiment of the invention, tourniquet article includes a self cinching buckle including a polygonal frame member and a self cinching member engaged with the frame member, the self cinching buckle is configured to have a constriction band threaded therethrough; and a hook member adapted for connection to a tourniquet base, the hook member includes a trough configured to engage the polygonal frame member.

As used herein "substantially," "generally,", "slightly" and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

BRIEF DESCRIPTION OF THE SEVERAL VIEWS OF THE DRAWINGS

The above and other objects, advantages and features of the present invention will be more readily apparent from the following description, when read in conjunction with the accompanying drawings wherein.

DETAILED DESCRIPTION OF THE INVENTION

Figure 1:
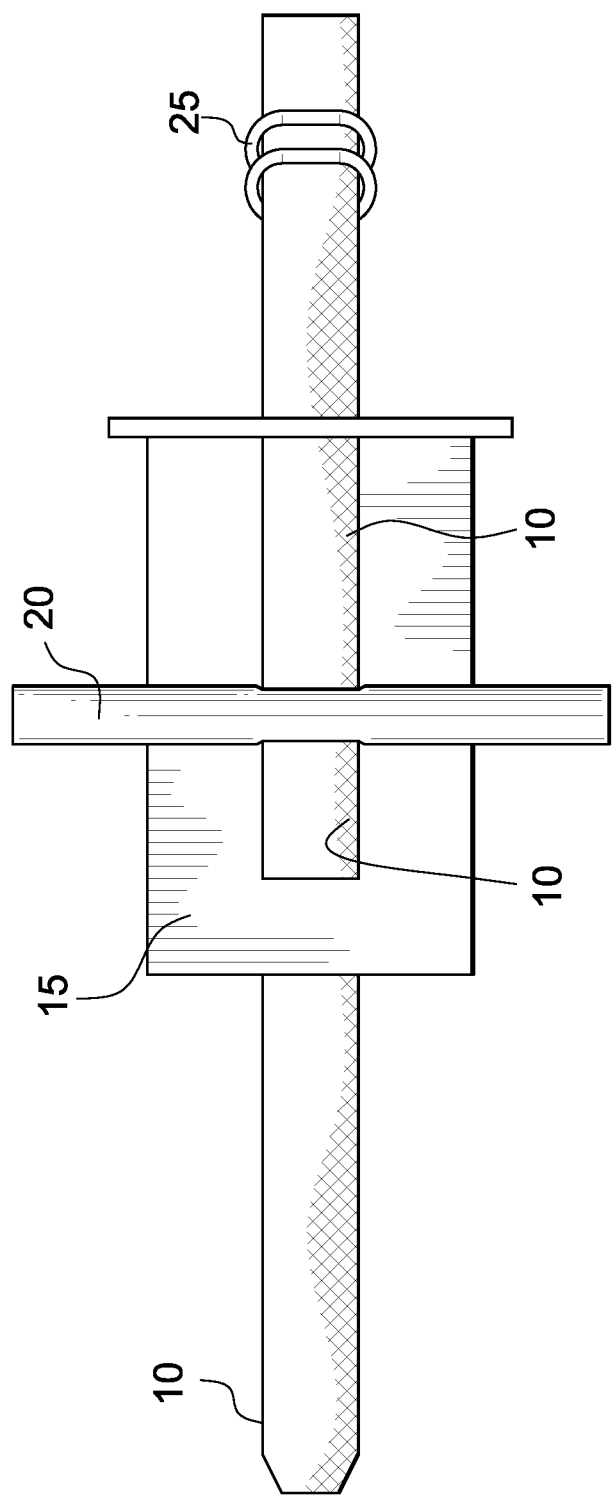
FIG. 1 is a plan view of an exemplary tourniquet.
Figure 2:
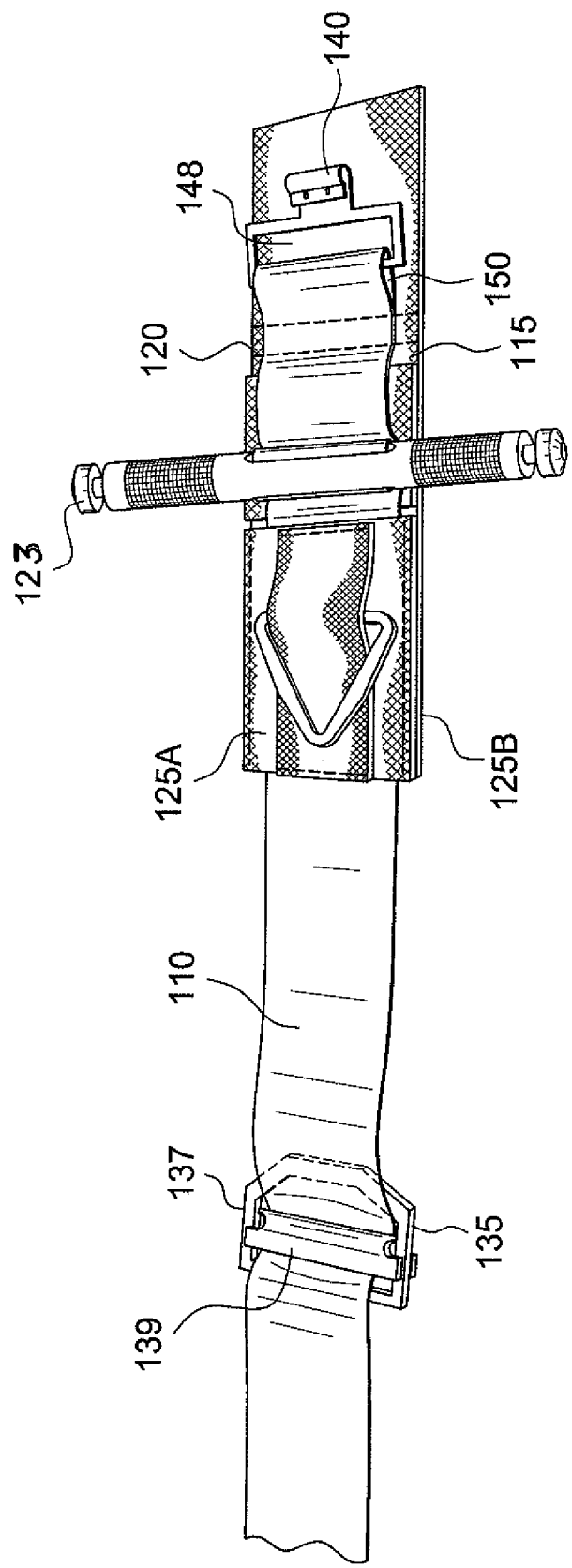
FIG. 2 is a perspective view of a tourniquet in accordance with an embodiment of the invention.

As illustrated in FIG. 2, the tourniquet according to the invention includes a constricting band 110 engaged with a base 115. Constricting band 110 preferably has a width of between about 1 inch and about 3 inches, more preferably a width of between about 1 inch and about 2 inches. In an exemplary embodiment, the constricting band has a width of about 1.5 inches.

A first end of constricting band 110 is fixedly attached, e.g., stitched, to base 115 at an attachment point 120. Constricting band 110 is then threaded through and/or engaged with a tourniquet handle 123 and reengaged with base 115 at a second end as illustrated in FIG. 2. For example, constricting band 110 may be sandwiched between upper and lower base layers 125A and 125B proximate to the second end of base 125. Constricting band 110 then extends from the second end of base 115 by at least a sufficient distance to allow constricting band 110 to be wrapped around the limb of an average size adult male. In some embodiments, tourniquet handle 125 may be attached to base 115 in the manner described in U.S. Pat. No. 7,776,064 which is herein incorporated by reference.

Figure 3:
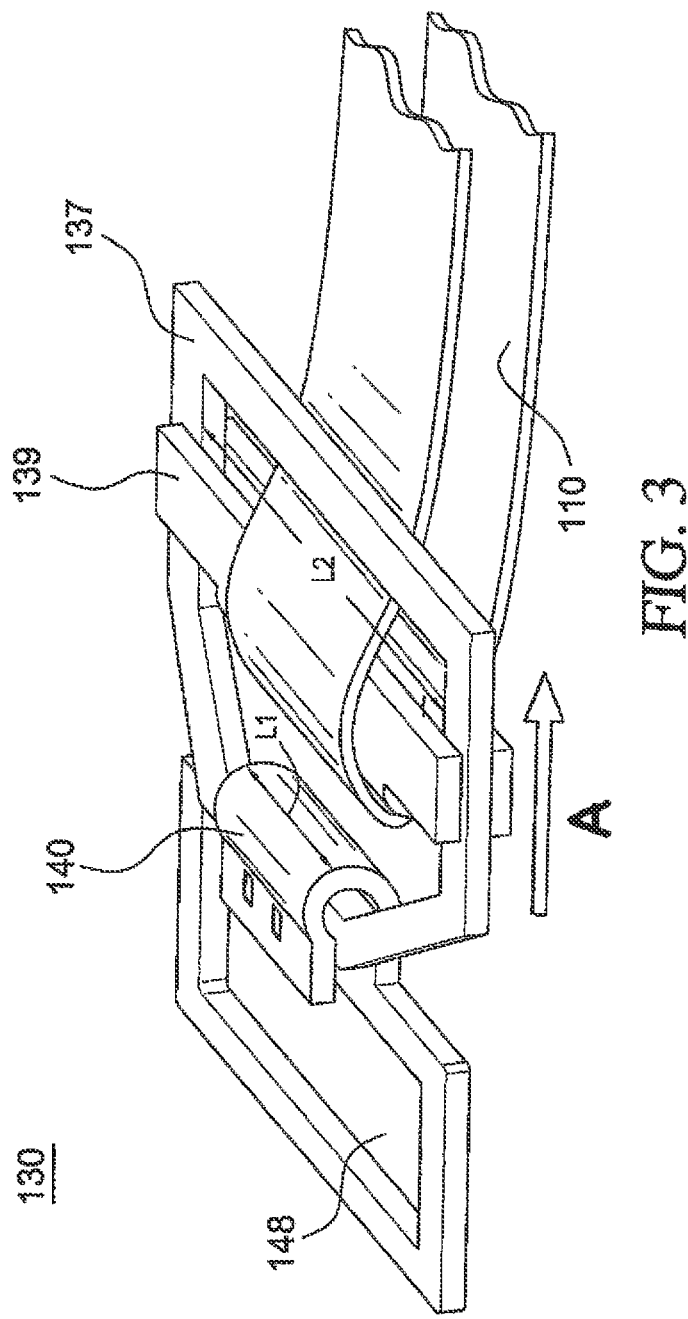
FIG. 3 shows a locking assembly for the tourniquet depicted in FIG. 2.

In accordance with the invention, an exemplary embodiment of the tourniquet according to this invention further includes locking assembly 130 comprising self cinching buckle 135 and hook member 140. In some embodiments, buckle 135 includes a polygonal frame member 137 having a self cinching member 139 engaged with polygonal frame member 137. As illustrated in FIG. 3, self cinching member 139 comprises a structural member such as a cuff or bar that extends across an opening of polygonal frame member 137 and forms a tongue and groove type engagement with first and second opposing sides of polygonal frame member 137. Constricting band 110 is looped around self-cinching member 139 such that by simply pulling the free end of constricting band 110 self-cinching member 139 slides along frame member 137 in the direction of arrow A until constricting band 110 is pinched between self cinching member 139 and frame member 137.

In the illustrated embodiment, frame member 137 is hexagonal. However, frame member 137 may comprise any polygonal shape that will allow self-cinching member 139 to pinch constricting band 110 against frame member 137.

Figure 4:
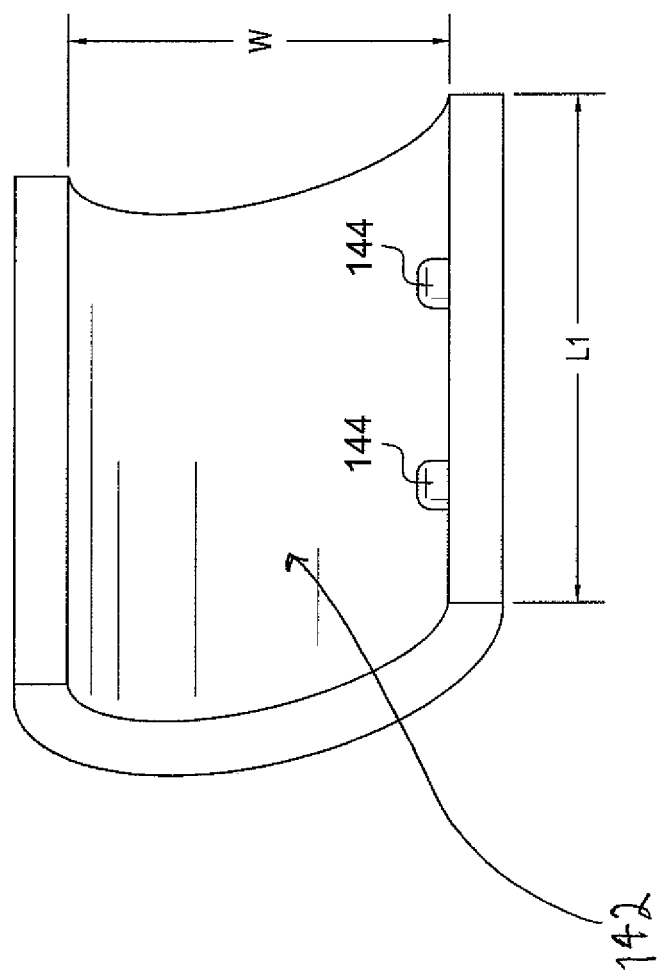
FIG. 4 depicts a top view of a hook member and strike interface of the locking assembly of FIG. 3.
Figure 5:
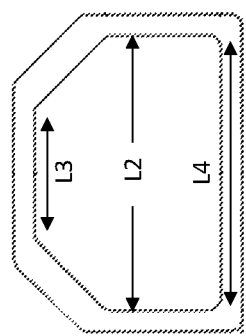
FIG. 5 depicts a top view of a frame member in accordance with an embodiment of the invention.

Hook member 140 is pivotally attached to constricting band 110 proximate to the first end of base 115 and is constructed to form a friction fit with frame member 137. As illustrated in FIG. 4, hook 140 comprises a cuff having an interior surface 142. Hook 140 has a lengthwise dimension L1 and width W. It is desirable to keep hook 140 engaged with frame member 137 unless and until a user actively disengages them. Accordingly, to prevent unintended disengagement that may occur, e.g., when the tourniquet is displaced by bouncing against a field medic, a first responder, a solider or hiker's equipment, interior surface 142 is provided with a strike interface comprising a plurality of protrusions 144. Protrusions 144 lock frame member 137 into hook member 140 and minimize accidental disconnection. In addition, protrusions 144 provide an audible alert, i.e., a click, when the user reconnects frame member 137 thus letting them know that the connection is secure.

In keeping with an aspect of the invention hook member 140 has a length L1 that is substantially smaller than a lengthwise dimension L2 of the opening of frame member 137. In one embodiment, L1=1/2 L2. Because the size of the opening of frame member 137 is larger than the length of hook member 140, it is easier for an individual under stress to connect hook member 140 to frame member 137 as it minimizes complicated motor movements and reduces the level of hand eye coordination required to connect hook member 140 to frame member 137. These are particularly important considerations in low light combat environments. In addition, the side of frame member 137 that engages hook member 140 has a length L3 that is just slightly longer than L1, i.e., a few centimeters or less. This makes it easier to connect hook member 140 to frame member 137 while minimizing undesired relative movement, sliding and/or pivoting, of hook member 140 with respect to frame member 137.

In keeping with another aspect of the invention, it is desirable to minimize the loosening of the tourniquet such as may happen, e.g., if the tourniquet is snagged during patient movement. Accordingly, a loop 150 is threaded through eyelet 148 and fixedly attached to base 115, e.g., by stitching, to connect hook member 140 to base 115. Frame member 137 has a rectangular cross section. Accordingly, when frame member 137 is lodged in the crescent trough of hook member 140, as the tourniquet is displaced during patient movement or tactical extraction, hook member 140 is inclined to pivot about loop 150 and is disinclined to pivot about frame member 137 which minimizes the prospect of accidental loosening of constriction band 110.

While the present invention has been illustrated and described by means of specific embodiments and alternatives, it is to be understood that numerous changes and modifications can be made without departing from the spirit and scope of the invention. Therefore, it should be understood that the invention is not to be limited in any way except in accordance with the appended claims and their equivalents.

What is claimed is:

1. A tourniquet comprising:
   a unitary base;
   a unitary constricting band disposed partially within the unitary base, the unitary constricting band extending from the unitary base and having a first end attached to the unitary base;

a handle engaged with said unitary constricting band;
a self cinching buckle including a polygonal frame member and a self cinching member engaged with the polygonal frame member, a free end of said unitary constricting band being threaded through said self cinching buckle, the self cinching member including a cuff disposed within and slidably engaged with the polygonal frame member such that pulling the free end of the unitary constricting band causes the self cinching member to slide along the polygonal frame member and pinch the unitary constricting band between the self cinching member and the polygonal frame member, the polygonal frame member including an opening having a lengthwise dimension L2; and
a hook member disengaged from the unitary base and directly pivotally attached to the first end of said unitary constricting band, the hook member having a hook configured to releasably engage said polygonal frame member, where a side of the polygonal frame member that engages said hook has a length L3 that is less than a length L4 of an opposing side of the polygonal frame member and said hook has a length L1 that is about one half of the lengthwise dimension L2 of the opening of the polygonal frame member,
wherein a first end of the unitary base extends beyond an entirety of the hook member in a direction opposite the handle.

2. The tourniquet of claim 1 wherein the self cinching member includes a bar disposed within and slidably engaged with the polygonal frame member.

3. The tourniquet of claim 1 wherein the self cinching member forms a tongue and groove engagement with the polygonal frame member.

4. The tourniquet of claim 1 wherein said hook forms a friction fit with said polygonal frame member.

5. The tourniquet of claim 1 wherein said hook includes an interior surface having a plurality of protrusions.

6. The tourniquet of claim 1 wherein the length L3 is greater than the length L1 of said hook.

7. The tourniquet of claim 6 wherein the side of the polygonal frame member that engages said hook has rectangular cross section.

8. The tourniquet of claim 1 wherein said hook member and said self cinching buckle are metal.

9. The tourniquet of claim 1, wherein the unitary base and the unitary constricting band are separate pieces of the tourniquet.

10. The tourniquet of claim 1, wherein the unitary constricting band extends within the unitary base until it engages with the handle.

11. The tourniquet of claim 1, wherein the tourniquet includes only one handle hook configured to engage with the handle.

12. The tourniquet of claim 1, wherein a portion of the polygonal frame member is formed as a bisected hexagon bisected at opposing vertices.

13. The tourniquet of claim 1, wherein the self cinching buckle is configured to slide laterally along the unitary constricting band.

14. The tourniquet of claim 13, wherein the self cinching buckle is configured to slide laterally from a second end of the unitary constricting band opposite the first end to a second end of the unitary base where the unitary constricting band enters the unitary base.

15. A tourniquet comprising:
a unitary base;
a unitary constricting band disposed partially within the unitary base, the unitary constricting band extending from the unitary base and having a first end attached to the unitary base;
a handle engaged with said unitary constricting band;
a self cinching buckle including a hexagonal frame member and a self cinching member engaged with the hexagonal frame member, a free end of said unitary constricting band being threaded through said self cinching buckle, the self cinching member being slidably engaged with the hexagonal frame member such that pulling the free end of the unitary constricting band causes the self cinching member to slide along the hexagonal frame member and pinch the unitary constricting band between the self cinching member and a first side of said hexagonal frame member; and
a hook member disengaged from the unitary base and directly attached to the first end of said unitary constricting band, the hook member including a cuff releasably engageable with a second side of said hexagonal frame member, the first side of said hexagonal frame member being parallel to the second side and the cuff having a length L1 that is shorter than a length L3 of the second side of the hexagonal frame member,
wherein a first end of the unitary base extends beyond an entirety of the hook member in a direction opposite the handle.

16. The tourniquet of claim 15 wherein the self cinching member includes a bar disposed within and slidably engaged with the hexagonal frame member.

17. The tourniquet of claim 16 wherein the self cinching member forms a tongue and groove engagement with the hexagonal frame member.

18. A tourniquet comprising:
a unitary base;
a unitary constricting band disposed partially within the unitary base, the unitary constricting band extending from the unitary base and having a first end attached to the unitary base;
a handle engaged with said unitary constricting band;
a self cinching buckle including a polygonal frame member and a self cinching member engaged with the polygonal frame member, a free end of said unitary constricting band being threaded through said self cinching buckle, the self cinching member being slidably engaged with the polygonal frame member such that pulling the free end of the unitary constricting band causes the self cinching member to slide along the polygonal frame member and pinch the unitary constricting band between the self cinching member and a first side of the polygonal frame member; and
a hook member disengaged from the unitary base and directly attached to the first end of said unitary constricting band, the hook member having a hook configured to releasably engage a second side of the polygonal frame member which is parallel to the first side,
wherein a first end of the unitary base extends beyond an entirety of the hook member in a direction opposite the handle.

19. The tourniquet of claim 18 wherein the second side of the polygonal frame member that engages said hook has a length L3 that is less than a length L4 of the first side of the polygonal frame member.

20. The tourniquet of claim 18 wherein the polygonal frame member includes an opening having a lengthwise dimension L2 and where a length of the hook L1 is about half of the lengthwise dimension L2.

21. A tourniquet comprising:
a base;
a constricting band disposed partially within the base, the constricting band extending from the base and having a first end attached to the base;
a handle engaged with said constricting band;
a self cinching buckle including a polygonal frame member and a self cinching member engaged with the polygonal frame member, a free end of said constricting band being threaded through said self cinching buckle, the self cinching member being slidably engaged with the polygonal frame member such that pulling the free end of the constricting band causes the self cinching member to slide along the polygonal frame member and pinch the constricting band between the self cinching member and a first side of the polygonal frame member; and
a hook member disengaged from the base and directly attached to the first end of said constricting band, the hook member having a hook configured to releasably engage a second side of the polygonal frame member which is parallel to the first side,
wherein a first end of the base extends beyond an entirety of the hook member in a direction opposite the handle.

22. The tourniquet of claim 21 wherein at least a portion of said base includes first and second layers and at least a portion of said constricting band is sandwiched between the first and second layers.

23. A tourniquet comprising:
a unitary base;
a unitary constricting band disposed partially within the unitary base, the unitary constricting band extending from the unitary base and having a first end attached to the unitary base;
a handle engaged with said unitary constricting band;
a self cinching buckle including a polygonal frame member and a self cinching member engaged with the polygonal frame member, a free end of said unitary constricting band being threaded through said self cinching buckle, the self cinching member including a cuff disposed within and slidably engaged with the polygonal frame member such that pulling the free end of the unitary constricting band causes the self cinching member to slide along the polygonal frame member and pinch the unitary constricting band between the self cinching member and the polygonal frame member, the polygonal frame member including an opening having a lengthwise dimension L2; and
a hook member disengaged from the unitary base and directly pivotally attached to the first end of said unitary constricting band, the hook member having a hook configured to releasably engage said polygonal frame member, where a side of the polygonal frame member that engages said hook has a length L3 that is less than a length L4 of an opposing side of the polygonal frame member and said hook has a length L1 that is about one half of the lengthwise dimension L2 of the opening of polygonal frame member.

* * * * *